United States Patent [19]

Nummy

[11] Patent Number: 5,654,429

[45] Date of Patent: Aug. 5, 1997

[54] METHOD FOR THE PREPARATION OF 3-AMINO-2-CHLORO-4-ALKYLPYRIDINES

[76] Inventor: Laurence John Nummy, 145 Fostertown Rd., Newburgh, N.Y. 12550

[21] Appl. No.: 473,421

[22] Filed: Jun. 7, 1995

Related U.S. Application Data

[63] Continuation of Ser. No. 154,827, Nov. 18, 1993, abandoned, which is a continuation-in-part of Ser. No. 977,962, Nov. 18, 1992, abandoned.

[51] Int. Cl.$^6$ .......................... C07F 9/58; C07D 409/04; C07D 213/81; C07D 213/34
[52] U.S. Cl. .................. 546/21; 546/270.1; 546/289; 546/295; 546/304; 546/307; 546/309; 546/310
[58] Field of Search ..................... 546/304, 284, 546/295, 307, 309, 310, 21, 270.1

[56] References Cited

U.S. PATENT DOCUMENTS

| | | | |
|---|---|---|---|
| 4,172,095 | 10/1979 | Steinman et al. | 564/440 |
| 4,209,464 | 6/1980 | Steinman et al. | 564/442 |
| 4,404,069 | 9/1983 | Goodin et al. | 205/438 |
| 4,480,130 | 10/1984 | Ku et al. | 564/440 |
| 4,493,755 | 1/1985 | Goodin et al. | 205/434 |
| 4,496,765 | 1/1985 | Ku et al. | 564/440 |
| 5,200,522 | 4/1993 | Grozinger et al. | 546/250 |

FOREIGN PATENT DOCUMENTS 0185128  6/1986  European Pat. Off. .

OTHER PUBLICATIONS

P. Claus, W. Vycudlilik and W. Rieder "Die basenkatalysierte Umlagerung von N–Aryl–S,S–dialkylsulfimiden zu o–Alkylthiolkylanilinen", *Monatsheft for Chemie*, 102, pp. 1571–1582 (1971).

P. Clause and W. Rider, "Zum Mechanismus der Umlagerung von N–Aryl–S,S–dimethylsufimiden zu o–Methylthiomethylanilnen"*Manatshefte für Chemie*, 103, pp. 1163–1177 (1972).

P. Gassman and D. Amick, "Exclusive Ortho Substitution of Phenols via [2,3]–Sigmatropic Rearrangements", *J. Med. Chem. Soc.*, 100, pp. 7611–7619, (1978).

*Primary Examiner*—Alan L. Rotman

[57] ABSTRACT

A process for the preparation of a 3-amino-2-chloro-4-alkylpyridine of the formula:

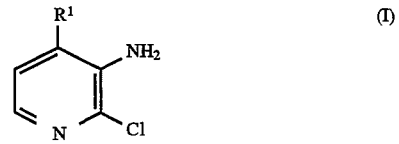

wherein R1 is a linear, branched or cyclic hydrocarbon of from one to eight carbon atoms, optionally substituted with one or more electron stabilizing groups, an intermediate in the preparation of certain 5,11-dihydro-6H-dipyrido[3,2-b:2',3'-e][1,4]diazepine compounds useful in the prevention and treatment of HIV infection.

13 Claims, No Drawings

METHOD FOR THE PREPARATION OF 3-AMINO-2-CHLORO-4-ALKYLPYRIDINES

RELATED APPLICATIONS

This application is a continuation of application Ser. No. 154,827, filed Nov. 18, 1993, abandoned which is a continuation-in-part of application Ser. No. 977,962, filed on Nov. 18, 1992 now abandoned

FIELD OF THE INVENTION

This invention relates to a novel method for preparing certain 3-amino-2-chloro-4-alkylpyridines.

BACKGROUND OF THE INVENTION

U.S. Pat. No. 5,200,522 published Apr. 6, 1993 discloses 2-Chloro-3-Amino-4alkyl-pyridine intermediates for preparation of "5,11 -Dihydro-6H-Dipyrido[3,2-b:2',3'-e][1,4] Diazepines and Their Use in the Prevention or Treatment of HIV Infection".

3-Amino-2-chloro-4-alkylpyridines are useful intermediates in the preparation of 4-alkyl-5,11 -dihydro-6H-dipyrido [3,2-b:2',3'-e][1,4]diazepines.

SUMMARY OF THE INVENTION

3-Amino-2-chloro-4-alkylpyridines prepared by the novel process of this invention have the formula:

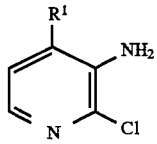

(I)

wherein $R^1$ is a linear, branched or cyclic hydrocarbon of from one to eight carbon atoms, optionally substituted with one or more electron stabilizing groups.

The process for this invention for the preparation of the compound of formula I is outlined below:

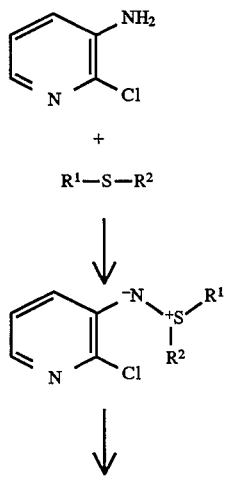

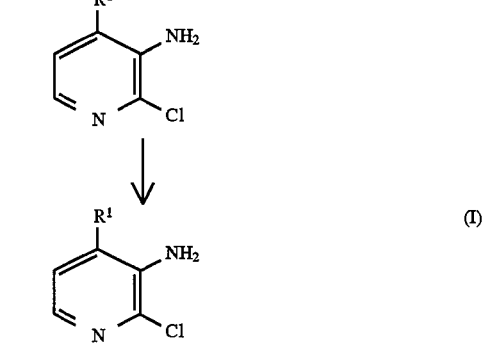

DETAILED DESCRIPTION OF THE INVENTION

The novel process of this invention for preparing the 3-amino-2-chloro- -alkylpyridine of formula I comprises the following steps:

Step 1, reacting a compound having the formula

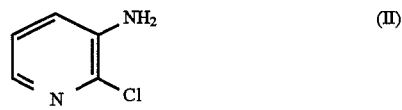

with a compound of the formula $R^1$-S-$R^2$, wherein (a) $R^1$ and $R^2$ are each a linear, branched or cyclic hydrocarbon of from one to eight carbon atoms; or (b) $R^1$ is a linear, branched or cyclic hydrocarbon of from one to eight carbon atoms, and $R^2$ is an aromatic or heteroaromatic group, such as phenyl, naphthyl, benzothiazolyl, benzoxazolyl, benzimidazolyl, pyridyl, furyl or thienyl; or (c) $R^1$ is a linear, branched or cyclic hydrocarbon of from one to eight carbon atoms, and $R^2$ is a linear, branched or cyclic hydrocarbon of from one to eight carbon atoms, wherein the carbon atom in $R^2$ bonded to the sulfur atom has no hydrogen bonded to it; or (d) $R^2$ is a linear, branched or cyclic hydrocarbon of from one to eight carbon atoms, and $R^1$ is a linear, branched or cyclic hydrocarbon of from one to eight carbon atoms optionally substituted with one or more electron stabilizing groups separated from the sulfur atom by one saturated carbon atoms substituted with at least one hydrogen atom; or (e) $R^1$ and $R^2$ are each a linear or branched hydrocarbon of from one to eight carbon atoms, joined together with the sulfur atom to form a ring of from 5 to 8 members, wherein the ring can optionally be substituted with one or more electron stabilizing groups separated from the sulfur atom by one saturated carbon atom substituted with at least one hydrogen atom, in the presence of an halogenating agent such as N-chlorosuccinimide, sulfurylchloride, chloramine-T, trichloroisocyanurate, chlorine, calcium hypochlorite, t-butyl hypochlorite, or the like, at a temperature ranging from $-60°$ C. to $25°$ C., for 1 to 24 hours, to produce a compound of the formula:

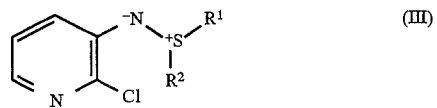 (III)

Examples of suitable electron stabilizing groups are $C_6$–$C_{10}$ aryl, $C_1$–$C_8$ carboalkoxy, carboxyamido, cyano, $C_1$–$C_{10}$ acyl (derived from aromatic or alkyl carboxylic acids), nitro, $C_1$–$C_8$ alkoxy, phosphoryl, $C_1$–$C_8$ alkyl, or $C_6$–$C_{10}$ arylthio, arylsulfinyl or arylsulfonyl.

Preferably, $R^1$ and $R^2$ are each a linear, branched or cyclic hydrocarbon of from one to eight carbon atoms.

More preferably, $R^1$ is a linear hydrocarbon of from one to four carbons and $R^2$ is a linear, branched or cyclic hydrocarbon of from one to eight carbon atoms.

Most preferably, $R^1$ is methyl or ethyl and $R^2$ is methyl, phenyl or 2-benzothiazolyl.

Step 2, heating the compound produced in Step 1 in the presence of (i) triethylamine, methanesulfonic acid, and an organic solvent such as toluene; or (ii) an organic solvent such as toluene, and a phenol of the formula:

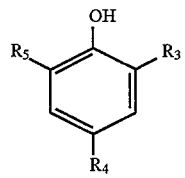

wherein $R_3$, $R_4$ and $R_5$ can each be H, $C_1$–$C_8$ straight chain or branched alkyl, Cl, Br or $CH_2SR_2$, wherein $R_2$ is as defined above;

$R_4$ can be —$C(CH_3)_2$—A, —$C(CH_3)$—$A_2$, $OR_6$, wherein $R_6$ is $C_1$–$C_8$ straight chain alkyl, —$[CH_2CH_2O]_n$—$CH_2CH_2OH$ and n is number from 0 to 20, and A has the formula:

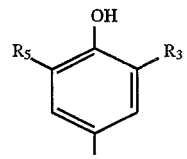

$R_5$ can be —$CH_2$—B, wherein B has the formula

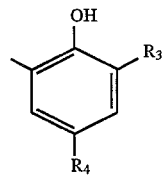

wherein $R_3$ is as defined above and $R_4$ can be as defined above, provided that it does not contain the group A, or a phenol of the formula

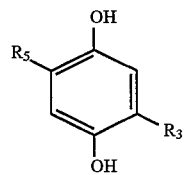

wherein $R_3$ is as defined above and $R_5$ is H or $R_3$, at a temperature ranging from 60° C. to 110° C., for 3 to 24 hours, to produce a compound of the formula:

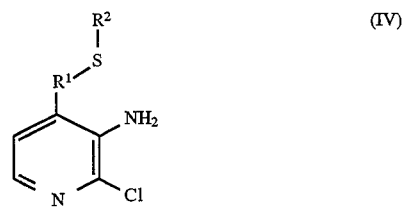 (IV)

Preferably, the phenol is selected from the group consisting of 2-6-di-t-butyl-4-methylphenol, 2-t-butyl-4-methylphenol or 2-t-butyl-4-methyl-6-methylthiomethylphenol.

Most preferably, the phenol is 2-t-butyl-4-methylphenol (BHT).

Step 3, heating the compound produced in step 2 in the presence of ethanol and Raney nickel at a temperature ranging from 25° C. to 80° C., for 1 to 24 hours, to produce the compound of formula I.

Alternatively, Step 3 comprises alkylating the compound produced in step 2 in the presence of an alkylating agent, at a temperature ranging from 20° C. to 100° C., for 1 to 140 hours, to produce a sulfonium salt and then contacting the sulfonium salt so produced with zinc at a temperature of 0° C. to 50° C., for 1 to 24 hours, to produce the compound of formula I.

Preferably, the alkylating agent is selected from the group consisting of methyl iodide, dimethylsulfate, allyl chloride, benzyl chloride, benzyl bromide, methyl chloride or chloroacetic acid..

Most preferably, the alkylating agent is dimethylsulfate.

Example 1 illustrates the preparation of the 3-amino-2-chloro-4- alkylpyridines of formula I.

EXAMPLE 1

Preparation of 3-Amino-2-Chloro-4-Methylpyridine

A) Preparation of S,S-Dimethyl-N-(3-Pyridyl) Sulfilimine

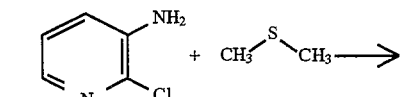

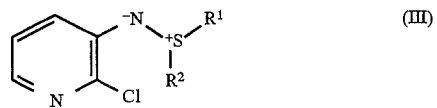

Prior to use, all glassware was dried in an oven at 105° C. and cooled either in a dessiccator or by venting to a nitrogen atmosphere while cooling. Dichloromethane was dried by storage over activated 4A molecular sieves.

A 3000 ml three-neck round bottom flask equipped with overhead mechanical stirrer and nitrogen inlet stopcock was charged with 3-amino-2-chloropyridine, 44.27g (0.34 moles). The apparatus was maintained under a slight positive pressure of nitrogen until the work up. Dichloromethane, 347 ml, dried by standing over activated 4A molecular sieves, was then introduced to the flask. Stirring was initiated and the flask was cooled until the internal temperature was −28° C., to produce a first slurry. Methyl sulfide, 25.68g (0.41 moles) was then added to the slurry via syringe over two minutes. The internal temperature of the flask was then allowed to equilibrate at −20° C.

A solution of N-chlorosuccinimide was prepared as follows: A 1000 ml round bottom flask equipped with magnetic stir bar, was charged with N-chlorosuccinimide, 45.98g (0.34 moles), followed by dichloromethane, 950 ml. This flask was sealed with a rubber septum and purged with nitrogen to produce a second slurry. The second slurry was stirred for 1 hour and 20 minutes, producing a cloudy solution.

The cloudy solution of N-chlorosuccinimide was added dropwise to the first slurry for 1 hour and 50 minutes, to produce a first reaction mixture. The temperature of the reaction mixture was maintained at −20° C. During the addition of N-chlorosuccinimide, the reaction mixture first became homogeneous and then a precipitate formed. When the addition of N-chlorosuccinimide was complete, the reaction mixture was allowed to stir at −20° C. for an additional 22 hours. The reaction mixture was then quenched by transferring it, over 15 minutes, to a stirred solution of 10% aqueous sodium hydroxide, 995 ml, which had been previously cooled to −5° C, to produce a second reaction mixture. During the transfer of the first reaction mixture, the temperature of the second reaction mixture was maintained between 0° C. and −5° C. When the transfer of the first reaction mixture was complete, the second reaction mixture was stirred for an additional 10 minutes and then allowed to settle, to produce an aqueous layer and an organic layer. The aqueous layer and organic layer were separated. The aqueous layer was then extracted (while still cold) with two successive 250 ml volumes of dichloromethane. The two extracts were then dried over anhydrous sodium sulfate, 100g, filtered and then concentrated in vacuo, to give 62.15g of an off-white colored solid. The solid so produced was slurried with toluene, 50 ml, at ambient temperature and the resultant supernatant so formed was then removed. This step was repeated twice with 25 ml aliquots of toluene. Residual toluene was removed by rinsing the solid with hexane. The resultant solid was finally dried at 30° C. under vacuum. This provided 52.09g of S, S-dimethyl-N-(3-pyridyl)sulfilimine (80% yield).

The resultant solid was characterized by combustion analysis:

| | | |
|---|---|---|
| % C | Calculated 44.56 | Found 44.53 |
| % H | Calculated 4.81 | Found 4.78 |
| % N | Calculated 14.85 | Found 14.83 |
| % Cl | Calculated 18.79 | Found 19.09 |
| % S | Calculated 16.99 | Found 17.03 |

Proton NMR: 60 MHz; CDCl$_3$; ppm downfield shift from TMS ref: 2.75, (s), 6H; 7.2, (m), 2H; 7.8, (m), 1H IR: KBr pellet cm$^{-1}$; 3093-3001, 2910, 1560-1442 (Pyridine ring stretching), 1388, 954 and 917 (S-methyl deformation), 900 (N-S stretch), 778, 688, 731

Melting point: 107°–112° C. with decomposition (uncorrected)

B) Preparation of 3-Amino-2-Chloro-4-Methylthiomethylpyridine

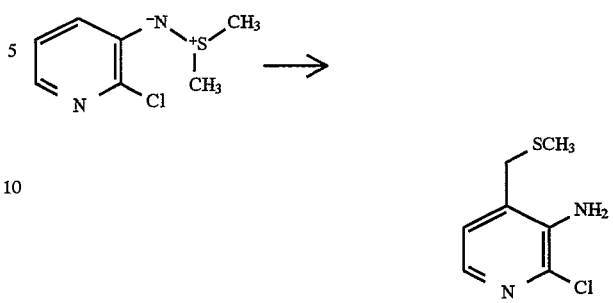

Prior to use, all glassware was dried in an oven at 105° C. and cooled either in a dessiccator or by venting to a nitrogen atmosphere while cooling. Toluene and triethylamine were also dried by storage over activated 4A molecular sieves.

i) A 100 ml three-neck round bottom flask equipped with a magnetic stir bar, reflux condenser and thermocouple, was charged with the S,S-dimethyl-N-(3-pyridyl)sulfilimine prepared in A (4.0 g, 21.2 mmoles) and 21 ml of toluene. The flask was purged with nitrogen and maintained under inert atmosphere. 14.6 ml (106 mmoles) of triethylamine was added to the flask with stirring over 5 minutes, to produce a reaction mixture. The reaction mixture was then heated to 85° C. for 23 hours. 1.4 ml (21.2 mmoles) of methanesulfonic acid was then added dropwise to the reaction mixture over 7 minutes, to produce a second reaction mixture. The second reaction mixture was heated at 85–90° C. for the remainder of 2 hours. The second reaction mixture was then allowed to cool to 25° C. 50 ml of water was then added to reaction mixture and stirred for 10 minutes, to produce an aqueous layer and a dark toluene layer. The aqueous layer is drained off and the dark toluene layer is extracted twice with 25 ml portions of water. The resultant dark toluene layer is then concentrated in vacuo to provide 3.2g of a dark oil. The oil is purified using silica gel flash chromatography (eluent: 6% ethyl acetate in dichloromethane (v/v)) to produce 2.2g (55%) of 3-amino-2-chloro-4-methylthiomethylpyridine ($R_f$=0.43).

The product so produced was characterized as follows:

Low Resolution CIMS: CH$_4$; m/z 153 (MH$^+$—HCl), m/z 141 (MH$^+$—CH$_3$SH)

Proton NMR: 270 MHz, CDCl$_3$, ppm downfield shift from TMS ref: 1.97, (s), 3H; 3.64, (s), 2H; 4.67, (brs), 2H; 6.92, (d, J=4.76 Hz), 1 H; 7.73, (d, J=4.76 Hz), 1H. N.O.E. enhancements SCH$_3$ at 1.97 ppm and NH$_2$ at 4.67 ppm; CH$_2$S at 3.64 ppm and NH$_2$ at 4.67 ppm.

$^{13}$C NMR: 68 MHz, CDCl$_3$, ppm downfield shift from TMS ref: 14.305, 34.029, 123.994, 130.172, 137.023, 137.472, 138.027

High Resolution MS: C$_7$H$_9$N$_2$$^{35}$ClS: Calculated 188.01749 Found 188,0170 C$_7$H$_9$N$_2$$^{37}$ClS: Calculated 190.01455 Found 190.0141 ii) A 1000 ml three-neck round bottom flask equipped with mechanical stirrer, reflux condenser and thermocouple, was charged with 100 g (530 mmoles)of the S,S-dimethyl-N-(3-pyridyl)sulfilimine prepared in A and 300 ml of toluene. 4.353g (26.5 mmoles) of 2-t-butyl-4-methylphenol and an additional 20 ml of toluene, were then added, to produce a reaction mixture. The flask was purged with nitrogen and maintained under inert atmosphere. The reaction mixture was heated to 85°–95° C. for 5 hours with stirring and then allowed to cool to ambient temperature. The dark toluene solution so produced is decanted from the tar and the decanted solution was then concentrated under reduced pressure to produce a dark oil weighing 98.26g. The yield of 3-amino-2-chloro-4-methylthiomethylpyridine was determined to be 68% by NMR analysis using trichloroethylene as internal standard. The crude product could be desulfurized without further purification.

C) Preparation of 3-Amino-2-Chloro-4-Methylpyridine

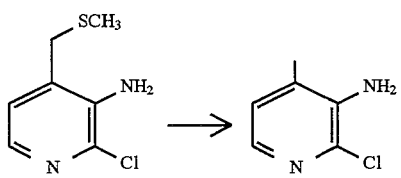

(i) A 12-liter three neck round bottom flask was equipped with mechanical overhead stirrer, inlet stopcock (tee-connected to nitrogen supply and oil bubbler vent) and type K thermocouple probe, to produce a reaction vessel. The reaction vessel was purged and maintained under nitrogen atmosphere. Grace 4200 Raney nickel, 2.71 Kg (dry basis), was charged to the vessel as a slurry in water. The resultant supernatant liquid in the vessel was transferred out of the vessel via 12 gauge line using nitrogen pressure, leaving a residue in the vessel. Methanol, 2.38 liters, was charged to the residue in the vessel and the resulting reaction mixture was stirred for 20 minutes. The stirring was terminated and the nickel in the reaction mixture was allowed to settle for 30 minutes. After the nickel settled, the resultant supernatant liquid was then transferred out of the vessel via 12 gauge line using nitrogen pressure. Stirring was resumed and a methanol solution (19.8% w/w) of crude 3-amino-2-chloro-4-methylthiomethylpyridine prepared as described in B above, was added over a one hour period via transfer line using nitrogen pressure, to produce a second reaction mixture. The internal temperature of the second reaction was maintained below 40° C. using a cool water bath. Fifty minutes after addition of the sulfide, TLC analysis of the second reaction mixture revealed that the desulfurization was complete. The second reaction mixture was then gently heated and a final reaction temperature of 51° C. was reached 1 hour 25 minutes after addition of sulfide. The second reaction mixture was then allowed to cool to ambient temperature overnight. Stirring was then discontinued, producing a reaction solution and a nickel residue. The reaction solution is transferred Out of the vessel via 12 gauge line using nitrogen pressure. The nickel residue was extracted three times, each time with 2.4 liters of fresh methanol, stirring for twenty minutes and then settling for one hour. The combined extracts were concentrated under reduced pressure and a maximum temperature of 65° C., producing a dark oil weighing 330 grams. The oil was taken up into 2.5 liters of toluene, filtered and concentrated again under pressure up to 65° C., producing a residue weighing 307 grams. This residue was purified by fractional distillation. The resultant pure distilled 3-amino-2-chloro-4-methylpyridine was characterized as follows:

Boiling point: 140° C./10 mmHg Melting point: 66°–68° C. (uncorrected)

Combustion analysis: Calculated % C, H, N, Cl: 50.54, 4.95, 19.65, 24.86 Found % C, H, N, Cl 50.54, 4.90, 19.73, 24.60

NMR: 250 MHz proton spectrum; CDCl$_3$ solvent; ppm downfield shift from TMS reference: 2.178, singlet, 3H; 4.173, hr. singlet, 2H; 6.899, doublet J=4.76 Hz; 1 H; 7.665, doublet J=4.74 Hz, 1H 68 MHz $^{13}$C spectrum; CDCl$_3$ solvent; ppm downfield shift (from 0.00 with 13CDCl3 reference at 76.996 ppm): 17.093, 124.49, 131.665, 136.302, 137.476, 138.099

Mass spectrum: low resolution Cl; methane; m/z, intensity: 143, 100; 145, 31.92 ii) 3-amino-2-chloro-4-methylthiomethylpyridine prepared above in B (90.2 mg, 0.48 mmoles) was dissolved in trifluoroacetic acid (450 µl). To the resulting solution was added dimethylsulfate (57.1 mg, 0.452 mmoles) at ambient temperature and allowed to stand at ambient temperature for 68 hours, to produce an alkylation solution. A proton NMR spectrum of the alkylation solution revealed that complete alkylation had occurred. The alkylation solution was then evaporated to dryness and the resultant residue was twice dissolved in methanol and evaporated to dryness, to produce an amber oil weighing 306.8 mg. The oil was dissolved in methanol (500 µl) and stirred in an atmosphere of nitrogen at ambient temperature while zinc dust (63 mg, 0.98 mmoles) was added portionwise over two hours. After complete addition of the zinc dust, the resultant mixture was allowed to continue stirring for 21 hours. An aliquot of the mixture was then removed for analysis by thin layer chromatography (silica gel; 3% methanol/dichloromethane as eluant) which revealed highly selective conversion to 3-amino-2-chloro-4-methylpyridine had occurred. The mixture was then filtered and the filtrate was concentrated to produce a dry residue. The residue was partitioned between ether and water (2 ml each). The layers were separated and the aqueous phase was extracted three additional times with 2 ml portions of ether. The ethereal extracts were combined and dried with anhydrous sodium sulfate, filtered and concentrated at reduced pressure to give 3-amino-2-chloro-4-methylpyridine as an oil weighing 66.6 mg. The oil solidified on standing. Product identity is confirmed by comparison of its proton NMR and TLC chromatographic properties (5% ethylacetate/dichloromethane, R=0.45; 3% methanol/dichloromethane, R=0.70) with those of an authentic sample.

What is claimed is:

1. A method for the preparation of a compound of the formula

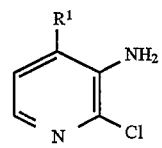

(I)

wherein R$^1$ is a linear, branched or cyclic hydrocarbon of from one to eight carbon atoms, optionally substituted with one or more electron stabilizing groups, which comprises:

a) reacting a compound of the formula

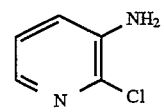

with a compound of the formula R$^1$—S—R$^2$, wherein R$^1$ and R$^2$ are each a linear, branched or cyclic hydrocarbon of from one to eight carbon atoms;

R$^1$ is a linear, branched or cyclic hydrocarbon of from one to eight carbon atoms, and R$^2$ is an aromatic or heteroaromatic group, such as phenyl, naphthyl, benzothiazolyl, benzoxazolyl, benzimidazolyl, pyridyl, furyl or thienyl; or R$^1$ is a linear, branched or cyclic hydrocarbon of from one to eight carbon atoms, and R$^2$ is a linear, branched or cyclic hydrocarbon of from one to eight carbon atoms, wherein the carbon atom in $R^2$ bonded to the sulfur atom has no hydrogen bonded to it; or $R^2$ is a linear, branched or cyclic hydrocarbon of from one to eight carbon atoms, and $R^1$ is a linear, branched or cyclic hydrocarbon of from one to eight carbon atoms optionally substituted with one or more electron stabilizing groups separated from the sulfur atom by one saturated carbon atoms substituted with at least one hydrogen atom; or R1 and R2 are each a linear or branched hydrocarbon of from one to eight carbon atoms, joined together with the sulfur atom to form a ring of from 5 to 8 members, wherein the ring can optionally be substituted with one or more electron stabilizing groups separated from the sulfur atom by one saturated carbon atom substituted with at least one hydrogen atom, in the presence of an halogenating agent, at a temperature ranging from −60° C. to 25° C., for 1 to 24 hours, to produce a compound of the formula:

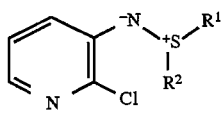

b) heating the compound produced in a) in the presence of: (i) triethylamine, methanesulfonic acid, and an organic solvent; or (ii) an organic solvent and a phenol of the formula:

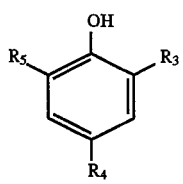

wherein $R_3$, $R_4$ and $R_5$ can each be H, $C_1$–$C_8$ straight chain or branched alkyl, Cl, Br or $CH_2SR_2$, wherein $R_2$ is as defined above;

$R_4$ can be —$C(CH_3)_2$—A, —$C(CH_3)$—A2, $OR_6$, wherein $R_6$ is $C_1$–$C_8$ straight chain alkyl, —[$CH_2CH_2O]_n$—$CH_2CH_2OH$ and n is number from 0 to 20, and A has the formula:

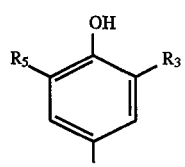

$R_5$ can be —$CH_2$—B, wherein B has the formula

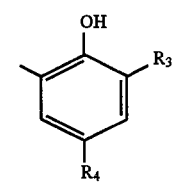

wherein $R_3$ is as defined above and $R_4$ can be as defined above, provided that it does not contain the group A, or a phenol of the formula

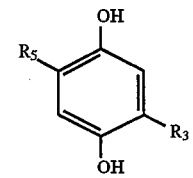

wherein $R_3$ is as defined above and $R_5$ is H or $R_3$, at a temperature ranging from 60° C. to 110° C., for 3 to 24 hours, to produce a compound of the formula:

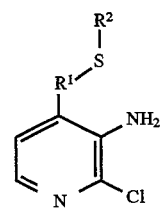

and c) heating the compound produced in b) in the presence of ethanol and Raney nickel, at a temperature ranging from 25° C. to 80° C., for 1 to 24 hours, to produce the compound of formula I.

2. A method as recited in claim 1 wherein $R^1$ and $R^2$ are each a linear, branched or cyclic hydrocarbon of from one to eight carbon atoms.

3. A method as recited in claim 2 wherein $R^1$ is a linear hydrocarbon of from one to four carbons and $R^2$ is a linear, branched or cyclic hydrocarbon of from one to eight carbon atoms.

4. A method as recited in claim 3 wherein $R^1$ is methyl or ethyl and $R^2$ is methyl, phenyl or 2-benzothiazolyl.

5. A method as recited in claim 1 wherein the phenol is selected from the group consisting of 2-t-butyl-4-methylphenol, 2,6-di-t-butyl-4-methylphenol or 2-t-butyl-4-methyl-6-methylthio-methylphenol.

6. A method as recited in claim 5 wherein the phenol is 2-t-butyl-4-methylphenol.

7. A method as recited in claim 1 wherein the one or more electron stabilizing groups are selected from group consisting of: $C_6$–$C_{10}$ aryl, $C_1$–$C_8$ carboalkoxy, carboxyamido, cyano, $C_1$–$C_{10}$ acyl (derived from aromatic or alkyl carboxylic acids), nitro, $C_1$–$C_8$ alkoxy, phosphoryl, $C_1$–$C_8$ alkyl, and $C_6$–$C_{10}$ arylthio, arylsulfinyl and arylsulfonyl.

8. A method as recited in claim 1 wherein b), the compound produced in a) is heated in the presence of triethylamine, methanesulfonic acid and an organic solvent.

9. A method as recited in claim 8 wherein the organic solvent is toluene.

10. A method as recited in claim 1 wherein in b), the compound produced in a) is heated in the presence of 2-t-butyl-4-methylphenol and an organic solvent.

11. A method as recited in claim 10 wherein the organic solvent is toluene.

12. A method as recited in claim I wherein in a), the halogenating agent is N-chlorosuccinimide, sulfurylchloride, chloramine-T, trichloroisocyanurate, chlorine, calcium hypochlorite, or t-butyl-hypochlorite.

13. A method as recited in claim 10 wherein the halogenating agent is N-chlorosuccinimide.

* * * * *

UNITED STATES PATENT AND TRADEMARK OFFICE
CERTIFICATE OF CORRECTION

PATENT NO.    : 5,654,429
DATED         : August 5, 1997
INVENTOR(S)   : Laurence John Nummy It is certified that error appears in the above-identified patent and that said Letters Patent is hereby corrected as shown below:

<u>Title page,</u>
Insert item: -- [73] Assignee:  Boehringer Ingelheim Pharmaceuticals, Inc. --

Signed and Sealed this

Twenty-sixth Day of August, 2003

JAMES E. ROGAN
*Director of the United States Patent and Trademark Office*